United States Patent
Yamagata

(10) Patent No.: US 8,632,606 B2
(45) Date of Patent: Jan. 21, 2014

(54) MEDICAL STENT

(75) Inventor: Toshihiro Yamagata, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/245,157

(22) Filed: Sep. 26, 2011

(65) Prior Publication Data

US 2012/0095545 A1 Apr. 19, 2012

Related U.S. Application Data

(63) Continuation of application No. PCT/JP2010/070197, filed on Nov. 12, 2010.

(30) Foreign Application Priority Data

Mar. 26, 2010 (JP) ................. P2010-073817

(51) Int. Cl.
*A61F 2/06* (2013.01)
*A61F 2/04* (2013.01)

(52) U.S. Cl.
USPC ...... 623/23.69; 623/1.36; 623/1.16; 623/1.22; 623/1.44; 623/1.34; 623/26.64; 623/23.65; 623/56.7; 623/23.71

(58) Field of Classification Search
USPC .......................... 623/23.64, 23.69–23.71, 1.34
See application file for complete search history.

(56) References Cited

U.S. PATENT DOCUMENTS

| | | | |
|---|---|---|---|
| 5,282,860 A | 2/1994 | Matsuno et al. | |
| 5,514,176 A | 5/1996 | Bosley, Jr. | |
| 6,093,199 A * | 7/2000 | Brown et al. | ......... 606/200 |
| 2004/0087886 A1 | 5/2004 | Gellman | |
| 2004/0230119 A1 | 11/2004 | Brustad et al. | |
| 2006/0195173 A1 | 8/2006 | DiMatteo | |
| 2008/0051911 A1* | 2/2008 | Rucker | ......... 623/23.7 |

FOREIGN PATENT DOCUMENTS

| | | |
|---|---|---|
| EP | 1 275 352 A2 | 1/2003 |
| JP | 05-192389 A | 8/1993 |
| JP | 2002-355316 A | 12/2002 |
| JP | 2004-147700 A | 5/2004 |
| JP | 2006-087712 A | 4/2006 |
| WO | WO 99/32051 A1 | 7/1999 |
| WO | WO 00/07524 A1 | 2/2000 |

OTHER PUBLICATIONS

International Search Report PCT/JP2010/070197 dated Feb. 15, 2011.
European Search Report dated Jul. 17, 2012 from corresponding European Patent Application No. EP 10 84 8473.4.

* cited by examiner

*Primary Examiner* — David Isabella
*Assistant Examiner* — Jacqueline Woznicki
(74) *Attorney, Agent, or Firm* — Scully, Scott, Murphy & Presser, P.C.

(57) ABSTRACT

A medical stent comprising a coil formed by winding a wire around an axis, an outer layer formed substantially tubular made from a first resin material, provided on an outer peripheral side of said coil and coaxial to said coil, and an inner layer formed substantially tubular made from a second resin material, provided on an inner peripheral side of said coil and coaxial to said coil.

8 Claims, 11 Drawing Sheets

MEDICAL STENT

The present application is a Continuation of International Patent Application No. PCT/JP2010/070197, filed Nov. 12, 2010, claiming priority on Japanese Patent Application No. 2010-073817, filed in Japan on Mar. 26, 2010, the contents of said Japanese Patent Application and said PCT Application being incorporated herein.

BACKGROUND OF THE INVENTION

1. Field of the Invention

The present invention relates to a medical stent.

2. Description of Related Art

Conventionally, a medical stent (hereinafter also abbreviated as 'stent') is placed to a stricture in a lumen inside a living body such as a blood vessel, a digestive tract, a bile duct, a pancreatic duct, and a urinary duct, in order to expand this stricture and maintain an open state.

A stent used in a bile duct such as that shown in Japanese Unexamined Patent Application, First Publication No. 2006-87712 is substantially tubular. Flaps which open in a natural state and can deform so as to close when a predetermined external force is applied, are provided on the distal-end side and the proximal-end side of this stent. The flaps engage with the entrance to the duodenal papilla and the end of the stricture of the bile duct, thereby preventing the stent from moving to the stricture.

Characteristics demanded of this type of stent include easy of bending in order to follow the curving shape of the bile duct in the body and the motion of the body, i.e. flexibility, and, at the same time, hardness (lumen-maintaining properties) so that it does not collapse when bent and can maintain the size of its own lumen.

One of this stent made from a soft resin (e.g. soft polyethylene, polystyrene elastomer, polyamide elastomer, polyester elastomer, polyurethane elastomer, etc.) formed in a tubular shape. While this can enhance the ease of bending of the stent, the thickness of the stent must be increased to prevent it from collapsing in the radial direction.

Another of the stent made from soft resin contains a blade which metal wire is woven like a mesh. In this case, when the stent is bent, the rigidity of the blade maintains the size of the lumen.

The stent is also required viewable under radioscopy. This is because the position of the stent needs to be confirmed by irradiation of X-rays when placing the stent or after placing it. It is important that both ends of the stent are astride the stricture to enable bile to reliably pass. And it is important that the flaps on the distal-end side of the stent reliably over the stricture to prevent the stent from moving (migrating, escaping) after it is placed. That is, it is necessary to confirm that the flaps are clearly open above the stricture and engaging with the stricture. When the stent has migrating into the bile duct, it must be removed while confirming its position under radioscopy. The proximal end of the stent is held with holding forceps or the like, whereby the stent is removed and collected. Therefore, in removing the stent, it is necessary that the whole stent can be seen under radioscopy, and that the proximal-end part of the stent can be confirmed clearly.

In placing the stent, there are cases where a plurality of stents are placed. In that case, it is important in this procedure to know the position of the first stent that was placed. Preferably, it is possible to see the whole stent, or to see its part other than both ends. This is to confirm whether the first stent is moving during subsequent stents procedures.

Japanese Unexamined Patent Application, First Publication No. 2004-147700 proposes a method of using a ring-like member or a plate-like member rounded to a substantially cylindrical shape to partially increase radioscopic visibility.

Japanese Unexamined Patent Application, First Publication No. H05-192389 proposes a medical stent made from an inner-layer material, a reinforcing layer, and an outer-layer material, with flaps formed only from the outer-layer.

SUMMARY OF THE INVENTION

According to a first aspect of the invention, a medical stent comprising a coil formed by winding a wire around an axis, an outer layer formed substantially tubular made from a first resin material, provided on an outer peripheral side of said coil and coaxial to said coil, and an inner layer formed substantially tubular made from a second resin material, provided on an inner peripheral side of said coil and coaxial to said coil.

Preferably, in the above medical stent, said first resin material of said outer layer is one of polyamide elastomer resin, polyethylene elastomer resin, polyethylene resin, polystyrene elastomer, or polyurethane elastomer resin, and in said outer layer, the Shore hardness is 25D or more and 70D or less, and the glass transition temperature is higher than −40° C.

Preferably, in the above medical stent, the flexural module of said outer layer is 5 MPa or more and 700 MPa or less, and the flexural module of said inner layer is 1000 MPa or less.

Preferably, in the above medical stent, the thickness of the stent is 0.20 mm or more and 0.35 mm or less, and, if Y1 is the maximum bending load (N) obtained in a cantilever stiffness test and X1 is the deflection (mm) when said maximum bending load Y1 was applied, indicator A defined by the following equation (1) is 4.0, or less.

$$A = \frac{Y1}{X1} \quad (1)$$

Preferably, in the above medical stent, said wire is formed from a radiopaque material, and said coil includes a marker coil part formed by winding said wire around said axis so that it is substantially close-wound, and a normal-wound coil part, which is connected to said marker coil part and is formed by winding said wire around said axis at a pitch that is two times or more and twenty times or less the pitch of said wire around the axis in said marker coil part.

Preferably, in the above medical stent, said wire is formed from a radiopaque material, a plurality of said coils are provided at difference positions on said axis, and adjacent coils among the plurality of said coils are connected by connection parts formed by wires parallel to said axis.

Preferably, in the above medical stent, further comprising an engaging member, whereof a first end is provided to an outer peripheral face of said outer layer, and whereof a second end extends said axis direction and can open to the outer side in the radius direction of the outer layer, said marker coil part of said coil is provided at a position corresponding to said second end of said engaging member in said axis direction.

Preferably, in the above medical stent, said marker coil part is additionally provided at a position corresponding to said first end of said engaging member in said axis direction, and said normal-wound coil part is connected to both of said marker coil parts.

Preferably, in the above medical stent, further comprising a bending part which is pigtail-shaped and formed at least one end part; and said marker coil part of said coil is provided so that it extends a predetermined length from an end of said bending part.

DETAILED DESCRIPTION OF THE INVENTION (First Embodiment)

A stent according to a first embodiment of the invention will be explained while referring to FIG. 1 to FIG. 9. The stent of this embodiment is placed in a bile duct of a living body by means of a stent delivery catheter or the like used percutaneously. In all the diagrams below, the ratios about the thickness or sizes of the constituent elements may differ from the actual sizes to facilitate understanding.

Figure 1:
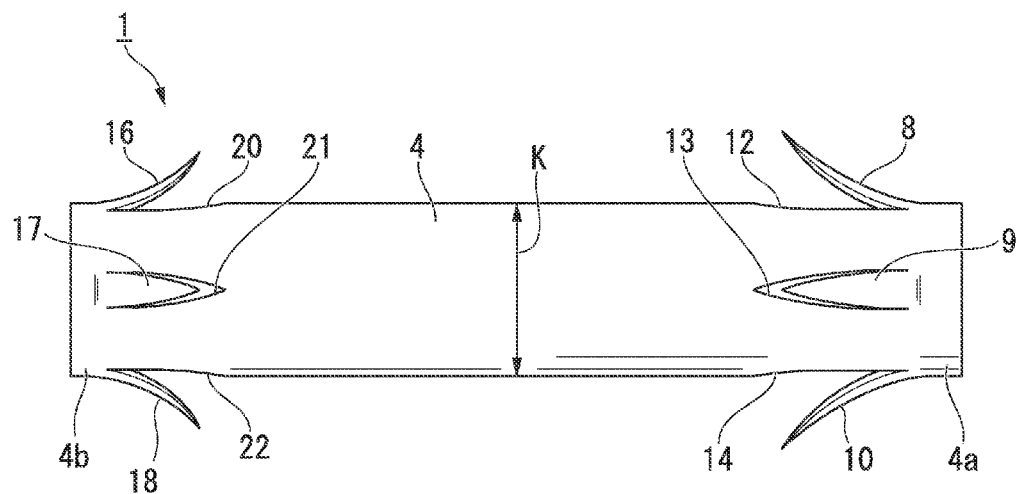
FIG. 1 is a side view of a stent in a first embodiment of the invention.
Figure 2:
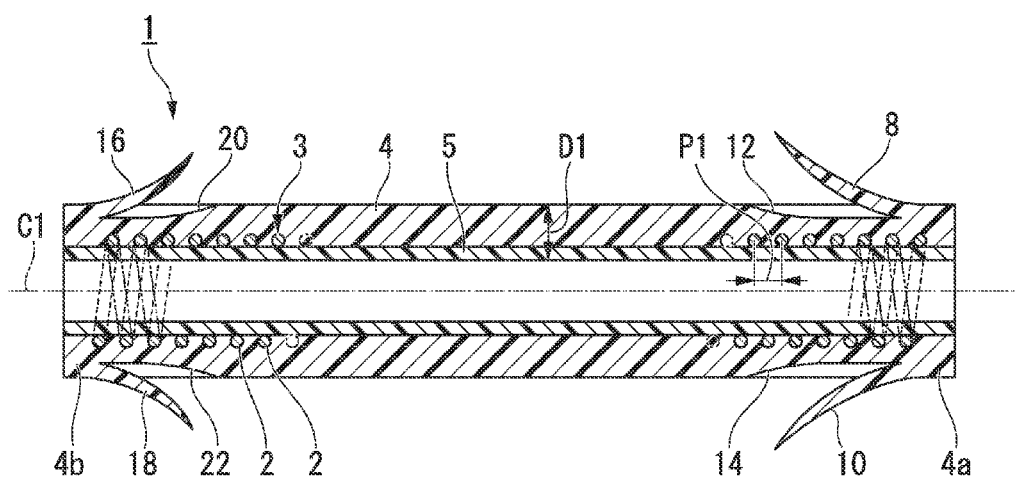
FIG. 2 is a cross-sectional view of primary parts of the same stent.

As shown in FIGS. 1 and 2, a stent 1 of this embodiment comprises a coil 3 formed by winding a wire 2 around an axis C1, an outer layer 4 which is formed substantially tubular and provided on the outer peripheral side of the coil 3 and coaxial to the coil 3, and an inner layer 5 which is formed substantially tubular and provided on the inner peripheral side of the coil 3 and is coaxial to the coil 3.

The wire 2 is made from a metal such as tungsten steel and stainless steel, which is a radiopaque material. The wire 2 is circular in cross section. This embodiment uses a wire 2, for example, with an outer diameter of 0.11 mm The wire 2 is wound in a coiled shape around the axis C1 to form the coil 3. If the distance between the cores of the wires 2 which are adjacent to each other in the direction of the axis C1 is treated as the pitch, in this embodiment, the wire 2 is wound at a pitch P1 of approximately 0.41 mm (with an interval between the wires 2 of approximately 0.30 mm)

The outer layer 4 is made from a polyurethane elastomer resin (first resin material)with a Shore hardness of 70D or less and a glass transition temperature higher than −40° C., and its nominal outer diameter K is 10 French (3.2 mm, hereinafter 'French' will be abbreviated as 'Fr'). The outer layer 4 is provided not only on the outer peripheral face of the coil 3 but also in the gaps between the wires 2.

The flexural module of the outer layer 4 is set at 700 MPa or less. While in this embodiment, the outer layer 4 is made from the polyurethane elastomer resin described above, the material for the outer layer 4 is not limited to this. The material for the outer layer 4 can suitably be used, for example, polyamide elastomer, polyethylene elastomer, soft polyethylene, polystyrene elastomer, polyester elastomer, or the like which have a Shore hardness of 70D or less and a glass transition temperature higher than −40° C.

Preferably, the flexural module of the outer layer 4 is 5 MPa or more, and the Shore hardness of the polyurethane elastomer, polyamide elastomer, soft polyethylene, polystyrene elastomer, polyester elastomer is 25D or more.

By using a soft material in this way, biocompatibility (the property which suitable for moving inside the body, flexibility and low resilient force) can be obtained. This has advantageous effects of suppressing migration and deviation of the stent, ulceration and the like, reducing pain for the patient (less invasiveness), etc.

The inner layer 5 is made from a material (second resin material) which is a fluorine resin and has elasticity, such as PFA (perfluoro alkoxyl alkane), FEP, or PTFE. The flexural module of the inner layer 5 is preferably 1000 MPa or less.

In this embodiment, the distance from the outer peripheral face of the outer layer 4 to the inner peripheral face of the inner layer 5, i.e. the thickness D1 of the stent 1, is set at 0.20 mm or more and 0.35 mm or less.

More specifically, the thickness of the inner layer 5 is 0.005 mm or more and 0.10 mm or less, and the thickness of the outer layer 4 is 0.07 mm or more and 0.34 mm or less. The thickness of the inner layer 5 and the thickness of the outer layer 4 are set with consideration for flexibility, elasticity, the size of the lumen, etc.

It is advantageous for collapse resistance, flexibility, reduction of wide lumens and outer diameter, etc. by setting these thickness.

On the outer peripheral face of the outer layer 4, on the side of a distal-end part 4a that becomes a distal-end side when inserted into the bile duct, four flaps (engaging member) 8-11 are provided at equal angles around an axis C1 (flap 11 is not shown). The flaps 8-11 are formed by cutting along a surface of the outer layer 4 without cut out and can be open at an end side of a flaps on parts of the distal-end part 4a of the outer layer 4.

The flaps 8-11 have elasticity, and when they are pressed toward the radially inward side of the outer layer 4, they are stored in notched parts 12-15 respectively (notched part 15 is not shown).

Similarly, four flaps 16-19 are provided at equal angles around the axis C1 on the outer peripheral face of a proximal-end part 4b of the outer layer 4 (flap 19 is not shown). The flaps 16-19 are formed by cutting along a surface of the outer layer 4 without cut out and can be open at an end side of a flaps on parts of the proximal-end part 4b of the outer layer 4. The flaps 16-19 are shorter in the direction of the axis C1 than the flaps 8-11.

By shortening the flaps on the proximal-end side (duodenum side) in this way, it is possible to prevent trouble caused by the flaps snagging on the forceps stand at the exit of the endoscope.

The length of the flaps 16-19 is preferably 10 mm or less. If the flaps 16-19 are longer than 10 mm, it is more difficult for them to pass through the forceps stand, making it more difficult to insert the stent.

The flaps 16-19 have elasticity, and when the flaps 16-19 are pressed toward the radially inward side of the outer layer 4, they are stored in notched parts 20-23 respectively (notched part 23 is not shown).

When the stent 1 configured in this manner is placed inside a body, it is important to ensure the resistance to collapsing and bending (kink resistance) of the stent 1 and the biocompatibility (the property which suitable for moving inside the body, flexibility and low resilient force) to maintain the size of the lumen despite flexion of the bile duct, moving, and the like. After the stent 1 has been placed inside the body, it is also important that it is not made to squash by pressure of a stricture, and that it is not buckling (break) when a stent was bent due to the bile duct is pulled along with the invasion of cancer. It is also important that the lumen is kept sufficiently wide.

Figure 3:
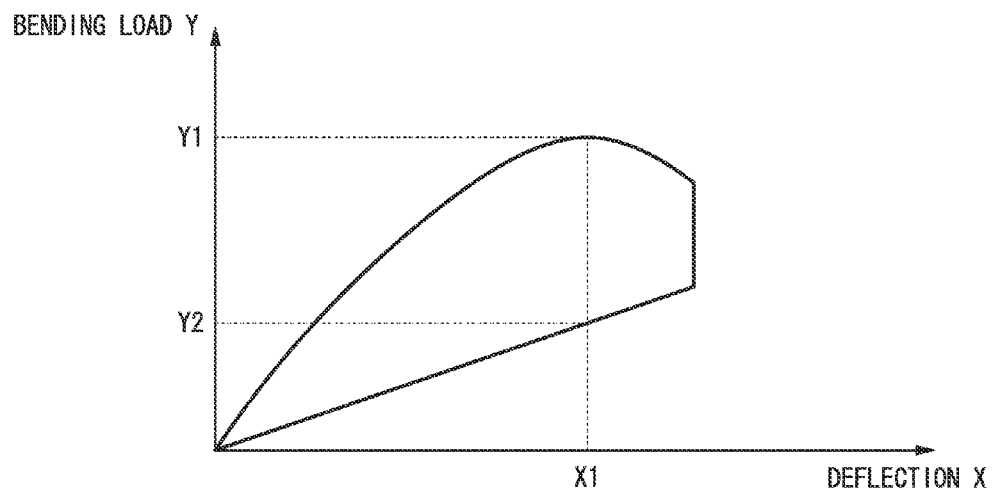
FIG. 3 is an explanatory diagram of the relationship between bending load and deflection when a cantilever stiffness test is carried out in an embodiments of the invention.

There are no established indicators for clearly showing the retention and flexibility of a lumen when a tubular stent is bent. Accordingly in this embodiment, a cantilever stiffness test was carried out as follows. As shown in FIG. 3, the indicators showing the measure of retention, flexibility, and width of the lumen are: the maximum bending load Y1 obtained in this cantilever stiffness test, the deflection X1 when the maximum bending load Y1 was applied, the resilient force Z that is the difference between the maximum bending load Y1 and the return bending load Y2 in the deflection X1, and the thickness D1 of the stent.

Of the data of result from the test, the deflection X1 was divided by the maximum bending load Y1 is indicator A. The resilient force Z was divided by the indicator A and converted to a percentage is indicator B.

That is, the resilient force Z, the indicator A, and the indicator B can be expressed with equations (2) to (4).

$$Z = Y1 - Y2 \quad (2)$$

$$A = \frac{Y1}{X1} \quad (3)$$

$$B = \frac{Z}{A} \times 100 \quad (4)$$

In the stent 1 of this embodiment, the indicator A, the indicator B, and the thickness D1 are preferably set. To set each one appropriately, for example, the thickness of the inner layer 5 is set at 0.005 mm or more and 0.10 mm or less, and the thickness of the outer layer 4 is set at 0.07 mm or more and 0.34 mm or less.

Figure 4:
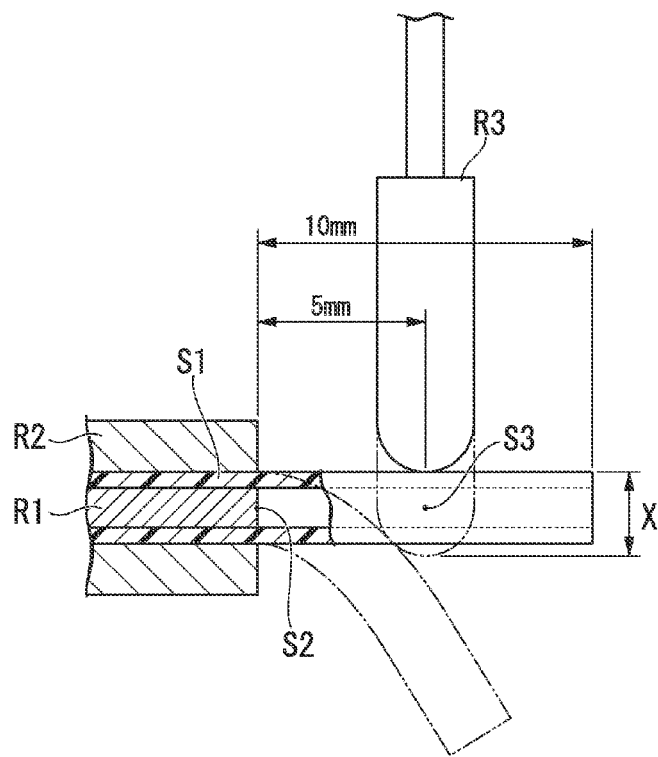
FIG. 4 is an explanatory diagram of a method of a cantilever stiffness test in an embodiments of the invention.

FIG. 4 is an explanatory diagram of a method of a cantilever stiffness test in an embodiment of the invention. It does not matter whether the stent S1 being tested has flaps or not.

A cylindrical core R1 having substantially the same diameter as the lumen in the stent S1 is inserted into the stent S1.

The range for inserting the core R1 is from the proximal-end side of the stent S1 to a position S2 which is 10 mm from the distal-end of the stent S1. The stent S1 is disposed horizontally, and the outer peripheral face of the section of the stent S1 corresponding to the range wherein the core R1 was inserted is wedged supported in a clamp R2.

Then, an attachment R3 is set such that the center of the attachment R3 abuts to the outer peripheral face of the stent 1 from above at a position S3 that is 5 mm from the position S2 on the distal-end side thereof. Then, while the attachment R3 is pressed vertically down at a speed of 5 mm per minute, to concurrently measure the deflection X when the attachment R3 is pressed down and the reactive force (the bending load Y) that the attachment R3 receives from the stent S1, by measuring apparatus (not shown). After pressing down the attachment R3 by 5 mm, it is returned in the opposite direction at the same speed, and the force received by the stent S1 is measured.

Figure 5:
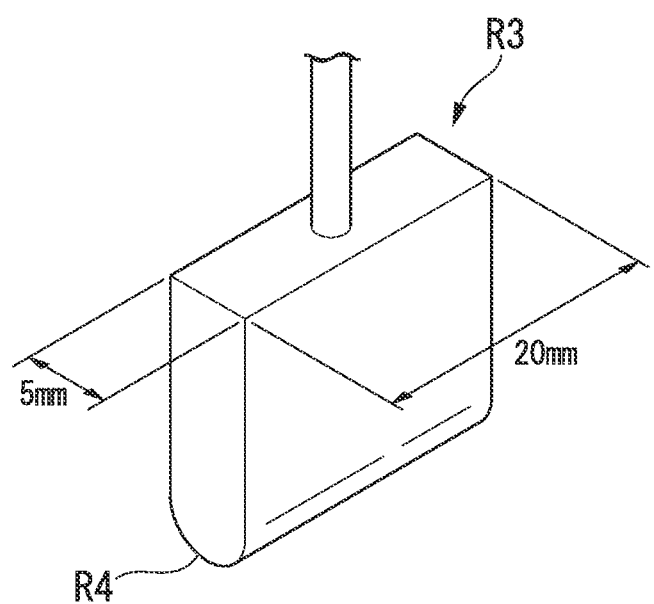
FIG. 5 is a diagram of an attachment used in a cantilever stiffness test in an embodiments of the invention.

As shown in FIG. 5, the attachment R3 has the shape of a plate with a width of 20 mm and a thickness of 5 mm. A contact face R4 of the attachment R3 to the stent S1 is curved with a radius of curvature of 2.5 mm, so that the bending load to the stent S1 does not concentrate at one point.

Figure 6:
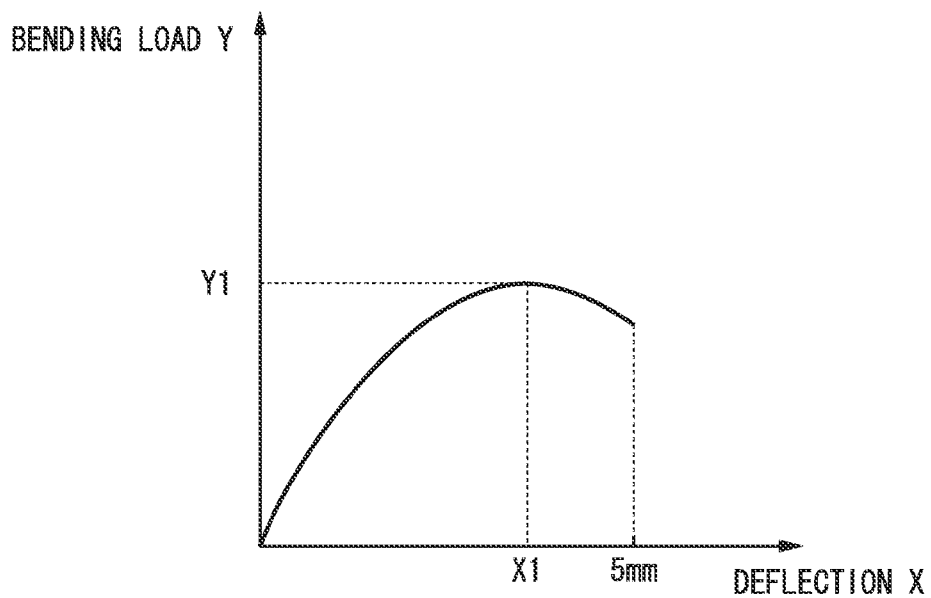
FIG. 6 is an explanatory diagram of one example of the relationship between bending load and deflection when a cantilever stiffness test is carried out in the first embodiment of the invention.

FIG. 6 is an example of results when the stent 1 of this embodiment was subjected to a cantilever stiffness test. In FIG. 6, the vertical axis represents the bending load Y, and the horizontal axis represents the deflection X. The deflection X of the stent 1 increased with increased amount of depression of the attachment R3, so the stent 1 reaches its maximum bending load Y1 at a deflection X1. And if the deflection X is increased any further, the bending load Y will start to decrease. The stent 1 bends as it follows, and, when the maximum bending load Y1 exceeds a predetermined level and no special member such as a reinforcing layer is provided for supporting the lumen, the stent 1 break.

The smaller the maximum bending load Y1, the more easily the stent will bend. The larger the maximum bending load Y1, the less easily the stent will bend (it has low flexibility). But, when the maximum bending load Y1 is small and the deflection X1 during the maximum bending load Y1 is below a fixed value, the stent breaks (kinks) during bending before the deflection X reaches 5 mm, whereby the lumen can no longer be maintained. On the other hand, the results show that even if the maximum bending load Y1 is small, when the deflection X1 during the maximum bending load Y1 is greater than a fixed value, the stent does not break during bending before the deflection X reaches 5 mm, and the lumen is maintained.

The results also show that when there is a smaller difference between the maximum bending load Y1 and the return bending load at the deflection X1 at the maximum bending load Y1, the resilient force is greater, i.e. the force for returning the stent to its original shape is greater.

When the indicator A is greater than a fixed value, the stent is less likely to bend (it is harder) and has weak lumen-maintaining properties during flexion. When the indicator A is less than a fixed value, the stent bends more easily (flexibly), yet its lumen-retention is still weak during flexion.

It is show that when the thickness D1 is greater than a fixed value, the inner diameter is small at a nominal size. And it is show that when the thickness D1 is smaller than a fixed value, the inner diameter is large at a nominal size.

The resilient force is greater when the indicator B is greater. When the indicator B is smaller, the stent is susceptible to plastic deformation. While it is preferable that the stent has a small indicator B, in practical terms this would reduce operability.

Thus the results show that the indicator A, the indicator B, and the thickness D1 have appropriate values as demanded for the stent.

As shown in FIG. 3, the upper limit of the maximum bending load Y1 demanded for the stent, the lower limit of the deflection X1 at the maximum bending load Y1, and the return bending load Y2 differ according to the nominal size K of the outer diameter of the stent (see FIG. 1).

The stent 1 of this embodiment has a nominal size K of 10 Fr, an inner diameter of φ2.8 mm, and an outer diameter of φ3.2 mm Preferably, the indicator A is less than 4 N/mm, the thickness D1 is 0.20 mm or more and 0.35 mm or less, and the upper limit of the indicator B is 70%.

When the stent 1 of this embodiment was subjected to a cantilever stiffness test, the indicator A was 1.29 N/mm, the thickness D1 was 0.24 mm, and the indicator B was 56%, showing that the stent 1 can achieve a larger lumen, can sufficiently maintain the lumen, and is flexible and little resilient force.

When the stent 1 of this embodiment was made with a different material and subjected to a cantilever stiffness test, the indicator A was 0.49 N/mm, the indicator B was 0.24 mm, and the indicator C was 50%, showing that the stent 1 can achieve a larger lumen, can sufficiently maintain the lumen, and is flexible and little resilient force.

Figure 7:
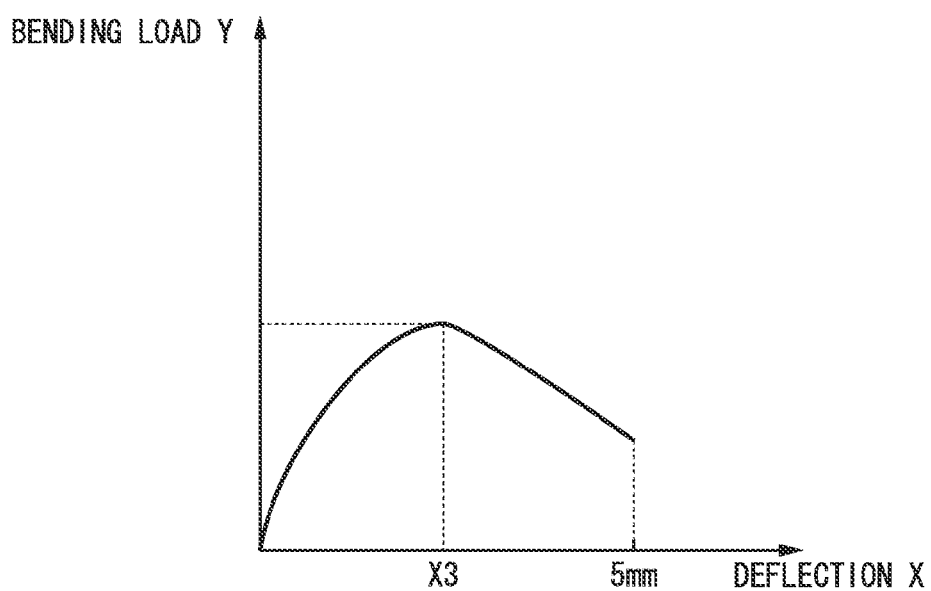
FIG. 7 is a diagram of the relationship between bending load and deflection when a cantilever stiffness test is carried out with a stent of a comparative example.

As a comparative example, FIG. 7 is an example of result obtained when a cantilever stiffness test was carried out to a conventional stent with a nominal size of 10 Fr and no coil.

The stent broke at a deflection X3 of less than 2.0 mm, and when the stent was bent until the deflection X reached 5 mm, the stent lumen became small.

A cantilever stiffness test was also carried out to a conventional stent using a reinforcing layer which is not a coil, e.g. a blade.

When the stent was bent to 5 mm, although the stent lumen did not become smaller, it did not follow the downward press of the attachment R3 and attained maximum load at a low deflection X3. The return bending load at the deflection X3 during maximum bending load was high.

The materials of the blade and the outer-layer part were replaced to make a flexible stent, and the test was again. The result was that, although the maximum load was greatly reduced, the stent lumen became smaller before 5 mm Also, there was plastic deformation, since the stent is not made only from flexible resin.

Subsequently, an operation of the stent 1 with the configuration described above will be explained, taking as an example a procedure for placing the stent 1 in a bile duct.

Figure 8:
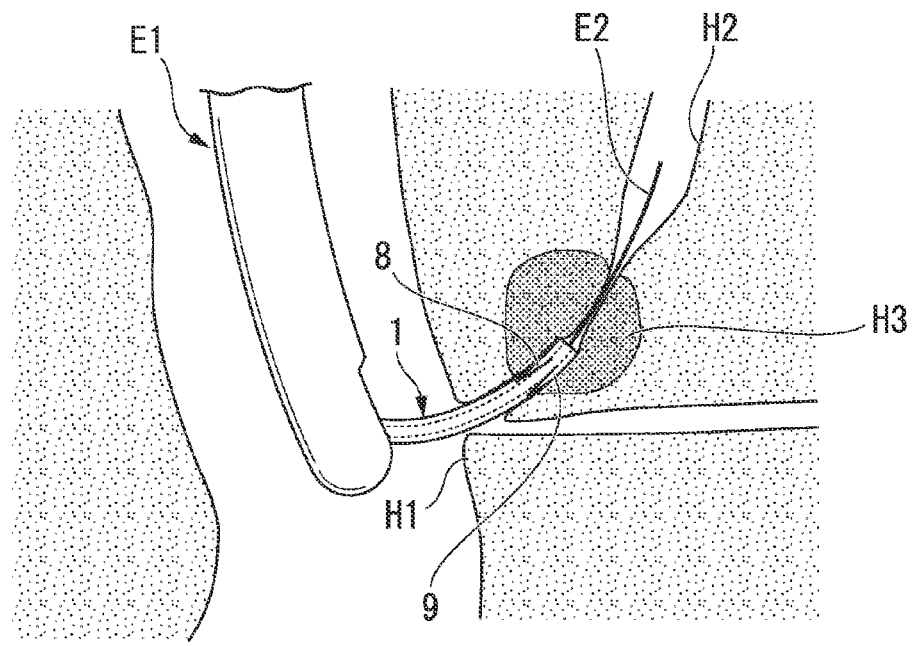
FIG. 8 is a diagram of an operation when using the stent of the first embodiment of the invention.

Firstly, the user inserts a side-view endoscope into the body of a patient through a natural opening such as his mouth, and, as shown in FIG. 8, advances the tip of the endoscope E1 to the vicinity of a duodenal papilla H1.

The user then inserts a guide wire E2 from a forceps opening (not shown) of the endoscope E1, and protrudes the tip of the guide wire E2 toward the duodenal papilla H1 while manipulating a forceps stand (not shown) as appropriate. The user then inserts the tip of the guide wire E2 from the duodenal papilla H1 into the bile duct H2.

Moreover, the user uses radioscopy to check the shapes of the duodenal papilla H1 and a stricture H3 of the bile duct H2, and selects a stent 1 whereof the length from the free ends of the flaps 8-11 to the free ends of the flaps 16-19 when the each flaps 8-11 and 16-19 are open exceeds the length from the duodenal papilla H1 to the stricture H3 of the bile duct H2.

The user insert the stent 1 from the distal-end (i.e. the flaps 8-11) side into the bile duct H2 along with guide wire E2 by using a stent delivery catheter (not shown) which is inserted from the forceps opening, while checking the positions and shapes of the stent 1 and the bile duct H2.

Figure 9:
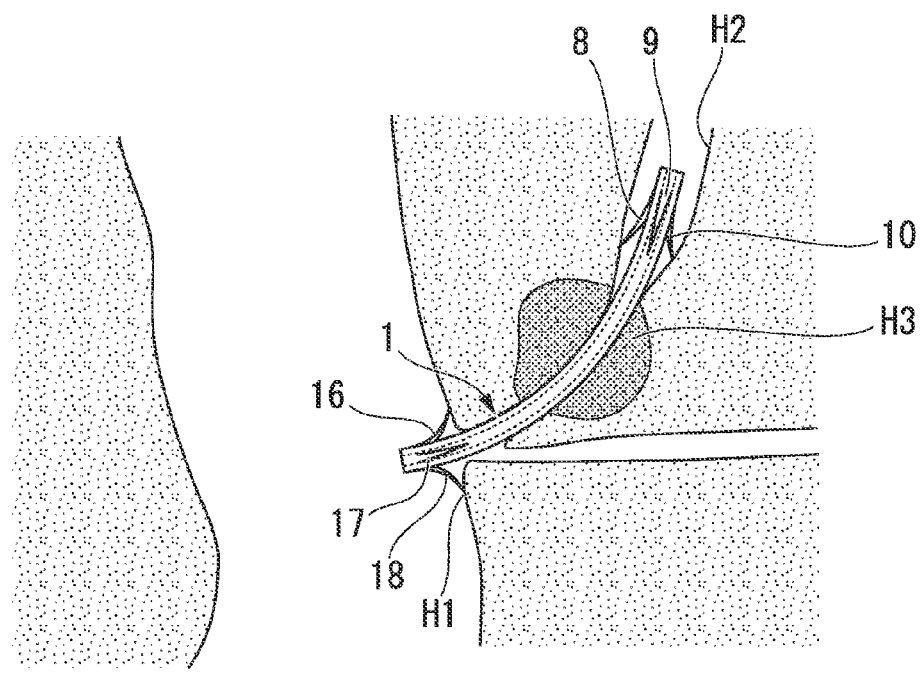
FIG. 9 is a diagram of an operation when using the stent of the first embodiment of the invention.

When the distal-end of the stent 1 reaches the stricture H3, the flaps 8-11 are pressed toward the axis C1 by the stricture H3 and stored in the notched parts 12-15 respectively. When the stent 1 is inserted further into the bile duct H2 and the flaps 8-11 through the stricture H3, the free ends of the flaps 8-11 are open, and the flaps 8-11 engage with the stricture H3, as shown in FIG. 9.

At this time, the flaps 16-19 also engage with the duodenal papilla H1 because it is selected a stent 1 wherein the length from the free ends of the flaps 8-11 to the free ends of the flaps 16-19 exceeds the length of the stricture H3.

Thereafter, the user removes the endoscope E1 from the body cavity of the patient, ending this series of procedures.

As described above, according to the stent 1 of this embodiment, since the coil 3 is provided between the outer layer 4 and the inner layer 5, the stent 1 is resistant to collapse in the radial direction, and can maintain the size of the lumen at all times, even if it is subjected to a bending load due to flexion of the bile duct, moving, change or the like.

Furthermore, since a blade is not used, it becomes possible to prevent it becoming thicker in the radial direction due to the wires 2 overlapping, and to prevent the stent 1 from becoming less easy to bend due to friction between the wires 2.

Since the outer layer 4 is made from a polyurethane elastomer resin with a bend elastic constant of 700 MPa or less, a Shore hardness of 70D or less, and a glass transition temperature is higher than −40° C., it is possible to prevent the outer layer 4 getting hard, and then, the overall stent 1 can be made easier to bend. Moreover, since the outer layer 4 is heated to around the body temperature while inside the body, it can be made more flexible.

Furthermore, the nominal outer diameter K of the outer layer 4 is 10 Fr, and the sizes and materials of the members of the stent 1 are set such that the value obtained by dividing the deflection from the maximum bending load is 0.3 N/mm or more and the thickness D1 is 0.35 mm or less. Therefore, the stent 1 can be made thin, i.e. so as to ensure a wide lumen, easy to bend, and collapse-resistant.

Since the stent 1 includes the flaps 8-11 and the flaps 16-19, it can engage with the stricture H3 of the bile duct H2, preventing problems such as migration and deviation of the stent 1.

By configuring the stent in the above manner, for example, the outer diameter (outer diameter of the outer layer 4) of a stent with an inner diameter (inner diameter of the inner layer 5) of 7.2 Fr (2.4 mm) can be reduced from 10.0 Fr (3.3 mm), which is the outer diameter of a conventional stent, to approximately 8.5 Fr (2.8 mm) The outer diameter of a stent with an inner diameter of 8.5 Fr (2.8 mm) can be reduced from the conventional 11.5 to 12.0 Fr (3.8 to 4 mm) to approximately 10.0 Fr (3.2 mm)

That is, according to the stent 1 of this embodiment, in comparison with a conventional stent, it is possible to provide a stent with the same inner diameter and a reduced outer diameter, and a stent with the same outer diameter and a larger inner diameter.

The coil 3 eliminates the need to use a large amount of contrast agent on the stent 1, thereby reducing a cause of physicality deterioration of the stent 1.

When the stent 1 has migrated, or when purposely using a procedure of inserting the proximal-end part 4b into the bile duct (inside stent), the coil 3 can be used to check the position of the proximal-end part 4b with X-ray radioscopy, making it easier to collect the stent 1.

(Second Embodiment)

Subsequently, a second embodiment of the invention will be explained. In this embodiment, like reference numerals are appended to like parts of the first embodiment, which are not repetitiously explained; only points of difference are explained.

Figure 10:
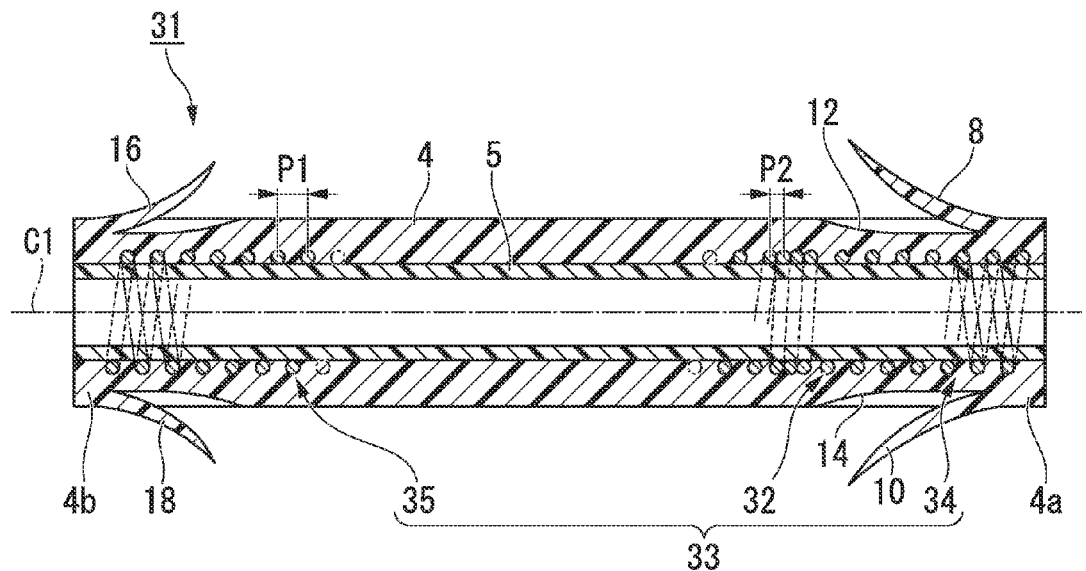
FIG. 10 is a cross-sectional diagram of primary parts of a stent in a second embodiment of the invention.

As shown in FIG. 10, a stent 31 of this embodiment includes a coil 33 comprising, a marker coil part 32 formed by winding a wire 2 at a predetermined position on an axis C1 of the coil 3 around that axis C1 so that it is substantially close coiling, and normal-wound coil parts 34 and 35 which are wound at the same pitch P1 as the wires 2 of the coil 3 of the first embodiment, instead of the coil 3 of the stent 1 of the first embodiment.

Here, 'close coiling' denotes that the wire is wound at a pitch with a fixed value that is greater than one times and seven times or less the outer diameter of the wire. For example, in this embodiment, which uses a wire 2 with an outer diameter of 0.11 mm, in the marker coil part 32, the gap between adjacent wires 2 is 0.01 mm to 0.08 mm, and the pitch P2 of the wires 2 is 0.12 mm to 0.19 mm At this time, the pitch P2 of the wires 2 is approximately 1.1 times to 1.7 times the outer diameter of the wires 2. To simplify the explanation, this gap is not shown in the drawings.

Due to the provision of this gap, in the marker coil part 32, the outer layer 4 and the inner layer 5 can be connected to each other in the section of the gap between adjacent wires 2, making them less likely to separate from each other.

If the size of the marker coil part 32 deviates from that described above, there will be no difference at radiopaque level between the coil pitch of the sparse part (i.e. the normal-wound coil) and the coil pitch of the close part (i.e. the marker coil part).

The length of the marker coil part 32 in the axis C1 direction is preferably 9 mm or less. This is in order to smoothly pass through the forceps stand of the endoscope opening. In a case where the freedom of the coil is fixed within a given range, if the length of the marker coil part 32 in the axis C1 direction is 9 mm or more, there is a possibility that it will be difficult for it to pass forceps stand when the forceps stand is stood.

The distal end of the marker coil part 32 is disposed such that it is at the same position as the proximal end of the notched part 12 in the axis C1 direction.

Sections of the coil 33 other than the marker coil part 32 are configured with the normal-wound coil parts 34 and 35, which are wound at the same pitch P1 (about 0.41 mm) as the wires 2 of the coil 3 of the first embodiment.

The pitch P1 of the wires 2 in the normal-wound coil parts 34 and 35 is preferably two times or more and twenty times or less the pitch P2 of the wires 2 of the marker coil part 32.

If the pitch P1 is less than two times the pitch P2, it becomes difficult to distinguish the marker coil part 32 from the normal-wound coil parts 34 and 35 under radioscopy. If the pitch P1 is more than twenty times the pitch P2, it becomes impossible to maintain the size of the lumen when the stent 31 is bent. Furthermore, the resin cannot enter into the gaps between the wires 2 wound at pitch P2, and that section consequently bulges.

The normal-wound coil part 34 is connected to the distal end of the marker coil part 32, and the normal-wound coil part 35 is connected to the proximal end of the marker coil part 32. The marker coil part 32, the normal-wound coil part 34, and the normal-wound coil part 35 constitute the coil 33.

When the stent 31 with this configuration is placed in the bile duct H2, under radioscopy, the radiopacity (X-ray shielding level) of the marker coil part 32 and the radiopacity of the normal-wound coil parts 34 and 35 are sufficiently different to be viewable. It is therefore possible to identify the interface between the marker coil part 32 and the normal-wound coil part 34, and the interface between the marker coil part 32 and the normal-wound coil part 35.

Figure 11:
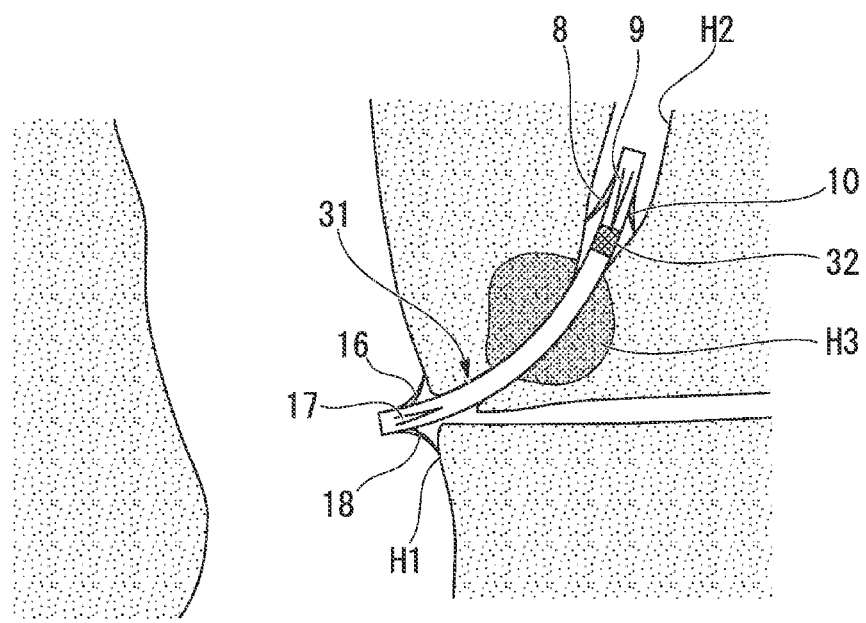
FIG. 11 is a diagram of an operation when using the stent of the second embodiment of the invention.

As shown in FIG. 11, under radioscopy, the user insert the stent 31 into the bile duct H2 while identifying the shape of the bile duct H2 and the position of the marker coil part 32 of the coil 33. The stent 31 is stopped inserting when the marker coil part 32 has passed beyond the stricture H3, the flaps 8-11 widen and engage with the stricture H3.

In the stent described in Japanese Unexamined Patent Application, First Publication No. 2006-87712 mentioned above, flaps are formed on the distal-end part and on the proximal-end part so that they open in a natural state. When the distal-end part of this stent is inserted into a stricture of a bile duct, the flaps formed on the distal-end part presses against the stricture and closes. When these flaps pass through the stricture of the bile duct, the closed flaps open and engage with the bile duct, thereby suppressing the remove of the stent toward the duodenal papilla side.

However, since the flaps of the stent cannot easily be viewed under radioscopy, it is difficult to determine whether they have opened and engaged with the bile duct. For this reason, if the stent is not inserted deeply into the bile duct, there are cases where the flaps fail to open and the stent slips out to the duodenal papilla side.

As described above, according to the stent 31 of this embodiment, the thickness can be suppressed to enable the stent 31 to bend easily, and, in addition, the stent 31 is always collapse-resistant, even if it is subjected to a bending load due to flexion of the bile duct, removing change, or the like, as in the stent 1 of the first embodiment.

Moreover, the pitch at which the wires 2 are wound is different in the marker coil part 32 than in the normal-wound coil parts 34 and 35. Therefore, when X-rays of a fixed intensity are irradiated to the coil 33, a difference is generated between the radiopacity of the marker coil part 32 and the radiopacity of the normal-wound coil parts 34 and 35. Under radioscopy, the positions of the distal ends (free ends) of the flaps 8-11 of the stent 31 can be viewed from this difference in intensity.

Since the positions of the distal ends of the flaps 8-11 can be viewed without using a large amount of contrast agent, the strength of the flap 8 can be increased. Also, a cause of physicality deterioration of the flap 8 can thereby be reduced.

Since the marker coil part 32 is provided in an intermediate part of the axis C1 direction of the stent 31, the whole stent 31 can be confirmed more clearly. When placing a plurality of stents, this is useful in placing the second and subsequent stents.

When the stent 31 travels inside the stricture H3 of the bile duct H2 from the distal-end part 4a side, the flaps 8-11 are pressingly engaged with the inner walls of the stricture H3, and their free ends move to the outer peripheral face side of the outer layer 4. At this time, the user can confirm the shape of the bile duct H2 and the position of the marker coil part 32 of the stent 31 under radioscopy.

Since the X-ray marker positioned near the flaps 8-11 is the marker coil part 32, it can bend flexibly in accordance with the bending of local parts.

The user advances the marker coil part 32 of the stent 31 past the stricture H3 of the bile duct H2 and into the bile duct 2, thereby the free ends of the flaps 8-11 is freed from the pressure that the stricture H3 is applying to the free ends of the flaps 8-11. Since the free end sides of the flaps 8-11 now open to the outer side in the radius direction of the outer layer 4 due to their own elasticity, the flaps 8-11 of the stent 31 engage with the deep side of the stricture H3 of the bile duct H2.

That is, the user advances the marker coil part 32, which can be identified under radioscopy, past the stricture H3 of the bile duct H2 and into the bile duct H2, thereby making the flaps 8-11 engage reliably with the deep side of the stricture H3 of the bile duct H2.

Figure 12:
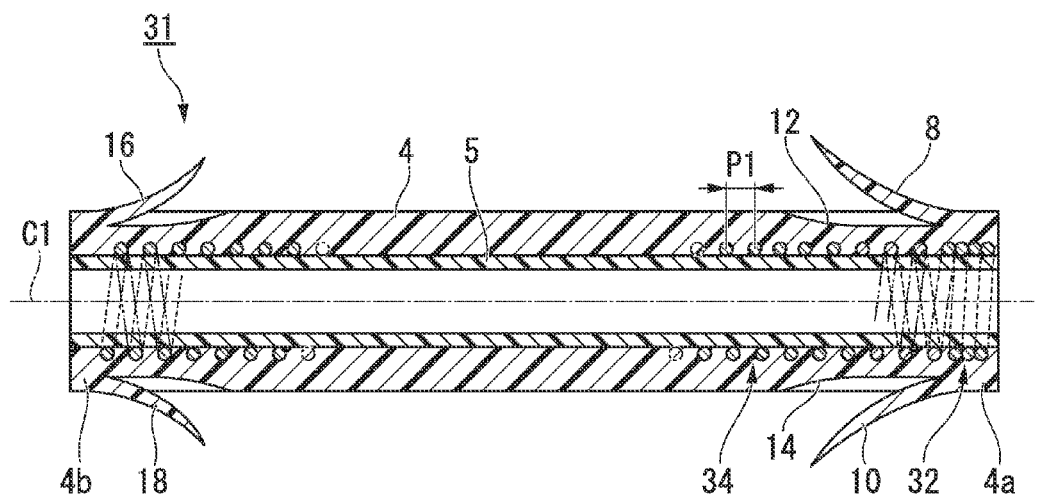
FIG. 12 is a cross-sectional view of primary parts of a stent in a modification of a second embodiment of the invention.

As shown in FIG. 12, the marker coil part 32 can be disposed such that its proximal end is at the same position as the distal end of the notched part 12 in the direction of the axis C1.

Figure 13:
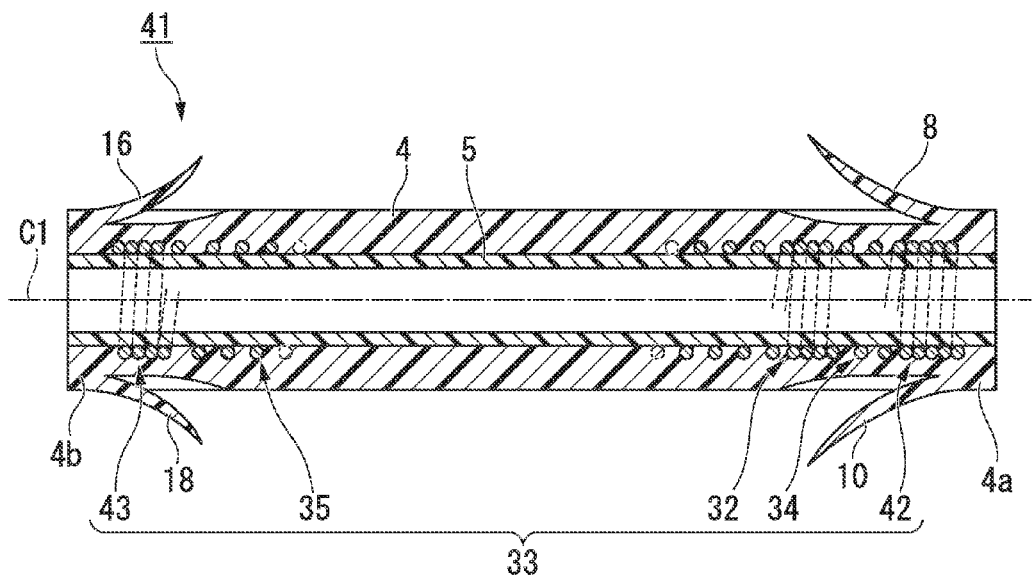
FIG. 13 is a cross-sectional view of primary parts of a stent in a modification of a second embodiment of the invention.

As in a stent 41 shown in FIG. 13, it is also acceptable to provide a marker coil part 42 and a marker coil part 43, formed from wires 2 wound around the axis C1 with close coiling in the same manner as the marker coil part 32, at both the distal end and the proximal end of the coil 33.

When the stent 41 is configured in this way, the positions of the distal end and the proximal end of the coil 33 can be reliably viewed under radioscopy by the marker coil parts 42 and 43.

The provision of the marker coil part 43 enables the force acting on the proximal-end part 4b side at the time of insertion to be transmitted efficiently to the distal-end part 4a side of the stent 41. There are two conceivable reasons for this: (1) the marker coil part 43 is strong against compression in the axis C1 direction, and (2) there is a small distance between the wires 2 in the close part (marker coil part) where the wires are wound more closely than in the spare part (normal-wound coil part) where they are wound comparatively sparsely, making it difficult for the resin to sufficiently fill the gaps between the wires 2. Reason (2) will be further explained below. The close part has a slightly larger outer diameter than the sparse part. The significance of this is that the area of the tube cross-section when transmitting the force from the proximal-end part 4b side to the distal-end part 4a side is large. Therefore, if the marker coil part 43 where the wires are comparatively close coiling is provided in the proximal-end part 4b, which is the side that directly receives the force, it will be easy to insert the stent 41.

(Third Embodiment)

Subsequently, a third embodiment of the invention will be explained. In this embodiment, like reference numerals are appended to like parts of the first and the second embodiments, which are not repetitiously explained; only points of difference are explained.

Figure 14:
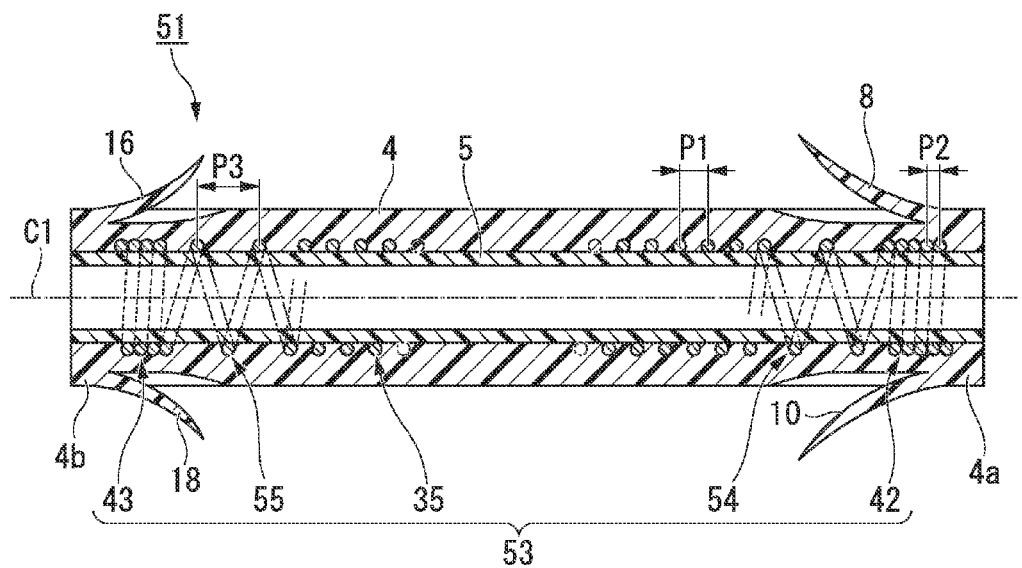
FIG. 14 is a cross-sectional view of primary parts of a stent in a third embodiment of the invention.

As shown in FIG. 14, a stent 51 of this embodiment includes a coil 53 instead of the coil 33 of the stent 41 of the modification of the second embodiment.

The coil 53 includes a normal-wound coil part 35, marker coil parts 42 and 43 provided at respective ends of the coil 53, a coarse-wound coil part 54 provided between the normal-wound coil part 35 and the marker coil part 42, and a coarse-wound coil part 55 provided between the normal-wound coil part 35 and the marker coil part 43.

Preferably, in this embodiment, the pitch P1 of the wires 2 in the normal-wound coil part 35 is two times or more and twenty times or less the pitch P2 of the wires 2 in the marker coil parts 42 and 43, while the pitch P3 of the wires 2 in the coarse-wound coil parts 54 and 55 is 1.1 times or more and 5 times or less the pitch P1 of the wires 2 in the normal-wound coil part 35.

Since the pitch of the wires 2 in the coarse-wound coil parts 54 and 55 is 1.1 times or more the pitch of the wires 2 in the normal-wound coil part 35, the interface between the coarse-wound coil part 54 and the normal-wound coil part 35, and the interface between the coarse-wound coil part 55 and the normal-wound coil part 35, can be viewed under radioscopy. Also, since the pitch of the wires 2 in the coarse-wound coil part 54 is two times or more the pitch of the wires 2 in the marker coil part 42, and the pitch of the wires 2 in the coarse-wound coil part 55 is two times or more the pitch of the wires 2 in the marker coil part 43, the interface between the coarse-wound coil part 54 and the marker coil part 42, and the interface between the coarse-wound coil part 55 and the marker coil part 43, can also be viewed under radioscopy.

The coarse-wound coil part 54 and the coarse-wound coil part 55 are provided in ranges with the axis C1 direction that nearly correspond to the flaps 8-11 and the flaps 16-19 respectively.

According to the stent 51 of this embodiment with this configuration, as in the stents of each of the embodiments, it is possible to suppress the thickness and maintain ease of bending, while making the stent collapse-resistant.

Moreover, the positions corresponding to the fixed ends and the free ends of each of the flaps 8-11 and the flaps 16-19 can be identified by viewing the interfaces between the adjacent coils under radioscopy.

(Fourth Embodiment)

Subsequently, a fourth embodiment of the invention will be explained. In this embodiment, like reference numerals are appended to like parts of the first to the third embodiments, which are not repetitiously explained; only points of difference are explained.

Figure 15:
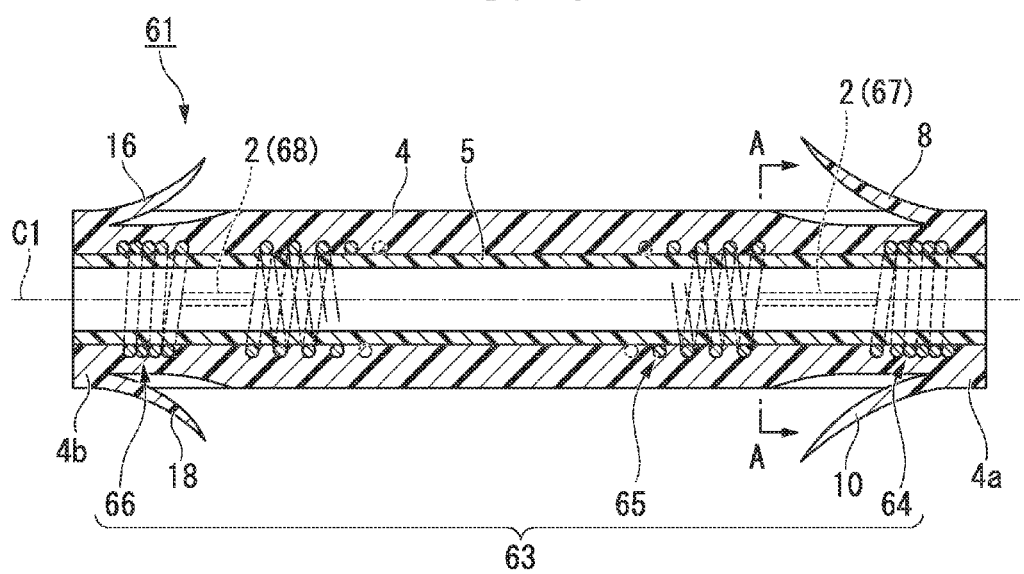
FIG. 15 is a cross-sectional view of primary parts of a stent in a fourth embodiment of the invention.

As shown in FIG. 15, a stent 61 of this embodiment includes a marker coil (coil) 64, a normal-wound coil (coil) 65, and a marker coil (coil) 66 at different positions on the axis C1, instead of the coil 53 of the stent 51 of the third embodiment.

The marker coils 64 and 66 are formed by winding the wires 2 around the axis C1 so that they are substantially close-wound at the pitch P2 in the same manner as the marker coil part 32 described above. The normal-wound coil 65 is formed by winding the wires 2 around the axis C1 so that it is normal-wound at the pitch P1 in the same manner as the normal-wound coil part 35 described above.

The normal-wound coil 65 and the marker coil 64 are connected to each other by a connection part 67, and the normal-wound coil 65 and the marker coil 66 are connected to each other by a connection part 68.

Figure 16:
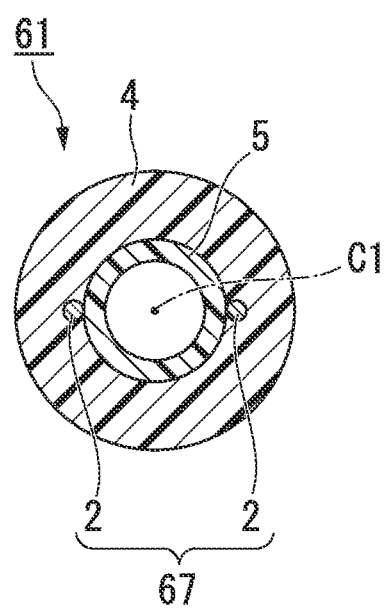
FIG. 16 is a cross-sectional view taken along the line A-A in FIG. 15.

As shown in FIGS. 15 and 16, the connection part 67 is formed from a group of wires 2 that are parallel to the axis C1. The wires 2 are disposed so that they are in line symmetry with the axis C1, with one end of each of the wires 2 connected to the marker coil 64, and the other end connected to the normal-wound coil 65. Any type of publicly known method can be used to connect the wires 2 to the marker coil 64 and to the normal-wound coil 65, such as soldering, spot welding, connection using a T-shaped joint member, etc.

The number and positions of wires 2 used for the connection part 67 can be set as appropriate.

Similar to the connection part 67, the connection part 68 is formed from one group of wires 2, with one end of each of the wires 2 connected to the marker coil 66, and the other end connected to the normal-wound coil 65.

According to the stent 61 of this embodiment with the above configuration, it is possible to suppress the thickness and maintain ease of bending, while making the stent collapse-resistant at all times, even if a bending load is applied to it due to flexion of the bile duct, traveling change, and such like.

Moreover, since the wires 2 of the connection parts 67 and 68 are disposed so that they extend along the axis C1, a force acting in the axis C1 direction at the distal-end part 4a can be efficiently transmitted to the proximal-end part 4b, and a force acting in the axis C1 direction at the proximal-end part 4b can be efficiently transmitted to the distal-end part 4a. By transmitting the forces in this manner, when to place the stent 61 inside the bile duct H2 by using a publicly known stent pusher, the force that the proximal-end part 4b of the stent 61 receives from the stent pusher is transmitted to the distal-end part 4a, enabling the stent 61 to be more easily inserted into the stricture H3 of the bile duct H2.

(Fifth Embodiment)

Subsequently, a fifth embodiment of the invention will be explained. In this embodiment, like reference numerals are appended to like parts of the first to the fourth embodiments, which are not repetitiously explained; only points of difference are explained.

Figure 17:
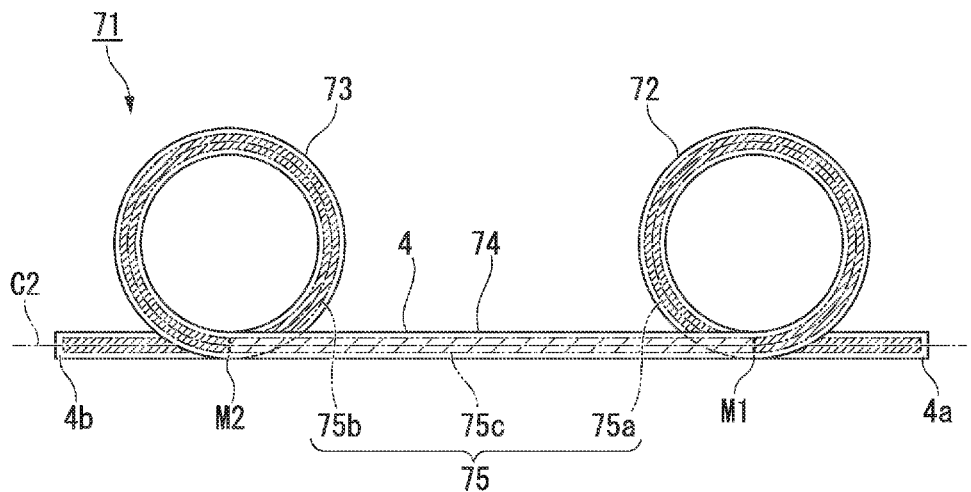
FIG. 17 is a side view of a stent in a fifth embodiment of the invention.

As shown in FIG. 17, a stent 71 of this embodiment has no flaps, and includes bending parts 72 and 73, which are formed in a so-called pigtail shape where they are rotated once so as to form a loop face parallel to an axis line C2, at the distal-end part 4a and the proximal-end part 4b. Sections sandwiched between the bending part 72 and the bending part 73 in the stent 71, i.e. sections adjacent to the bending part 72 and the bending part 73, form a main part 74.

A coil 75 described later is provided inside the outer layer 4, and the inner layer 5 described above (not shown) is provided inside the coil 75.

In the coil 75, a marker coil part 75a and a marker coil part 75b are respectively formed by winding wires 2 around the axis C2 at the same pitch P2 as the marker coil part 32 so that they are substantially close-coiling on the distal-end part 4a side from the interface M1 between the bending part 72 and the main part 74, and on the proximal-end part 4b side from the interface M2 between the bending part 73 and the main part 74. In a section sandwiched between the marker coil parts 75a and 75b, a normal-wound coil part 75c is formed by winding a wire 2 around the axis C2 at the same pitch P1 as the normal-wound coil part 35 described above.

According to the stent 71 of the embodiment with the configuration described above, the positions of the interfaces M1 and M2, and the positions of the distal-end part 4a and the proximal-end part 4b can be identified under radioscopy. Furthermore, due to color phase shading arising when the coil pitches are different, the interfaces can also be identified from their external appearances.

Figure 18:
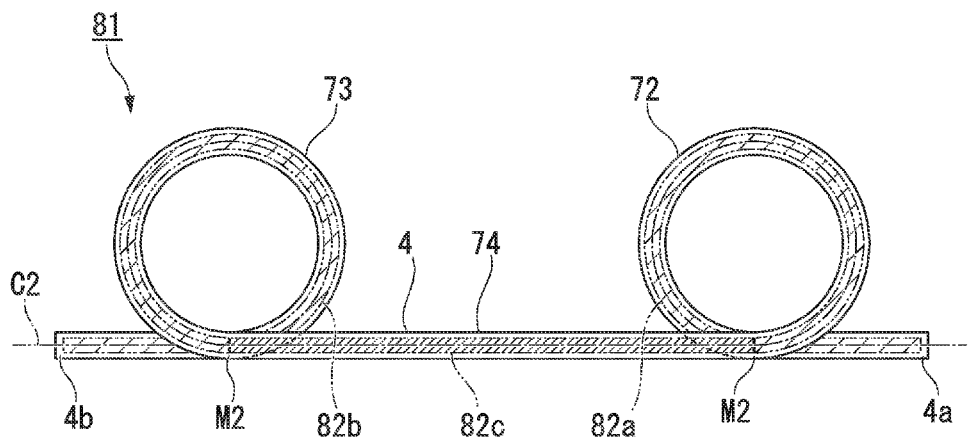
FIG. 18 is a side view of primary parts of a stent in a modification of a fifth embodiment of the invention.

As in a stent 81 shown in FIG. 18, instead of the marker coil part 75a and the marker coil part 75b of the stent 71 of the embodiment described above, a normal-wound coil part 82a and a normal-wound coil part 82b can be formed by winding the wire 2 around the axis C2 at the same pitch P1 as the normal-wound coil part 35; instead of the normal-wound coil part 75c, a marker coil part 82c can be formed by winding the wire 2 around the axis C2 at the same pitch P2 as the marker coil part 32, respectively.

Figure 19:
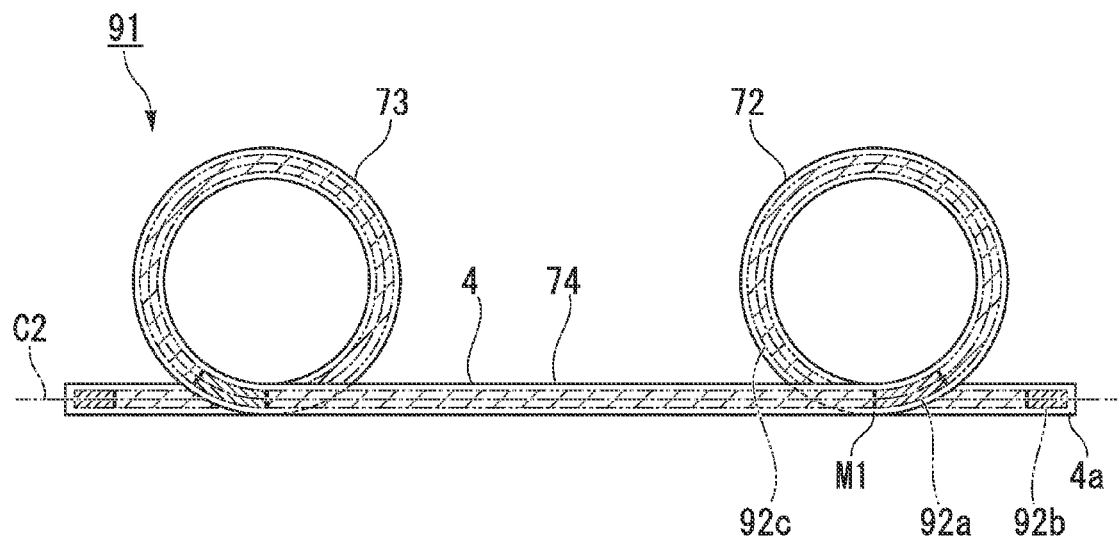
FIG. 19 is a side view of primary parts of a stent in a modification of a fifth embodiment of the invention.

As in a stent 91 shown in FIG. 19, instead of the marker coil part 75a of the stent 71 of the embodiment described above, marker coil parts 92a and 92b by winding wires 2 around the axis C2 at the same pitch P2 as the marker coil part 32 so that they are substantially close-wound, can be provided only at a predetermined distance from the interface M1 and a predetermined distance from the distal-end part 4a respectively, and a normal-wound coil part 92c by winding the wire 2 around the axis C2 at the same pitch P1 as the normal-wound coil part 35 described above, can be provided between the marker coil parts 92a and 92b.

The proximal-end part 4b side of the stent 91 can be configured in the same manner as the distal-end part 4a side.

Figure 20:
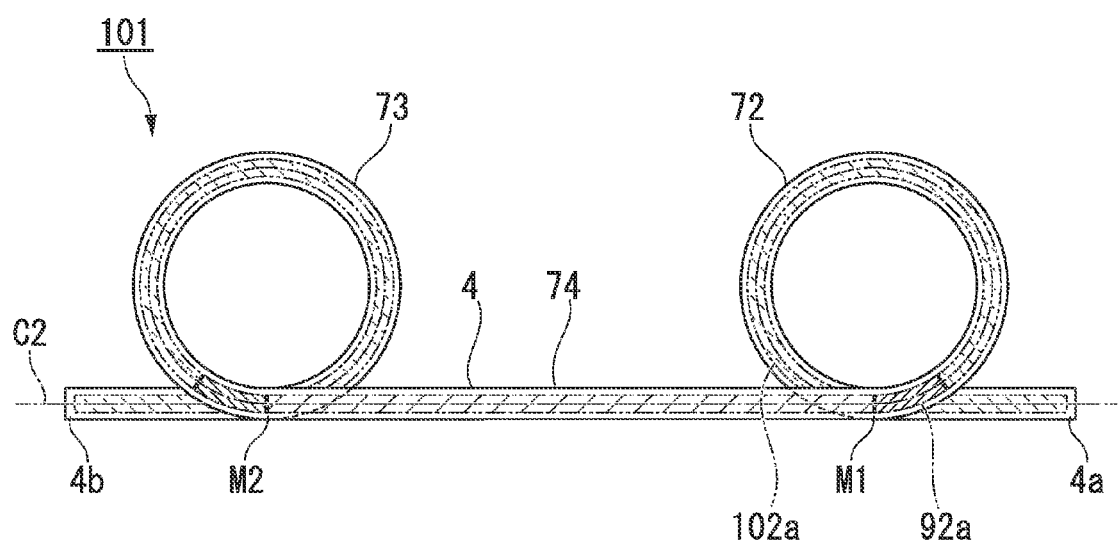
FIG. 20 is a side view of primary parts of a stent in a modification of a fifth embodiment of the invention.

As in a stent 101 shown in FIG. 20, instead of the marker coil part 92b and the normal-wound coil part 92c of the stent 91 of the modification described above, a coarse-wound coil part 102a can be provided by winding the wire 2 around the axis C2 at the same pitch as the coarse-wound coil part 54 described above.

The proximal-end part 4b side of the stent 101 can be configured in the same manner as the distal-end part 4a side.

While the first embodiment to the fifth embodiment of the invention have been described above with reference to the drawings, the specific configurations are not limited to these embodiments, and include changes to the configuration within a range that does not deviate from the main points of the invention.

For example, in the first embodiment to the fifth embodiment, a metal wire that is circular in cross-section is used as the wire 2. However, a wire that is square in cross-section can be spirally wound to form a flat coil. A stranded wire can also be used as the wire.

While in the first embodiment to the fifth embodiment, the coil 3 is configured from a single winding wire 2, a plurality of wires can be aligned in the radial direction and spirally wound to form a so-called multiple wound wire.

In the second embodiment to the fifth embodiment, the marker coil part is formed by winding the wire 2 so that it is substantially close coiling. However, the wire 2 can be close coiling, with no gap provided between adjacent wires 2 of the marker coil part.

Moreover, in the second embodiment to the fifth embodiment, the pitch of winding the wire 2 is changed to view the positions of connection sections of adjacent coils, the pitch can be kept fixed and the diameter of the wire changed instead.

While preferred embodiments of the invention have been described above, these are not limitative of the invention. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A medical stent comprising:
   a coil formed by winding a wire around an axis;
   an outer layer formed to be substantially tubular and made from a first resin material, wherein the outer layer is provided on an outer peripheral side of said coil and coaxial to said coil;
   an inner layer formed to be substantially tubular and made from a second resin material, wherein the inner layer is provided on an inner peripheral side of said coil and coaxial to said coil; and
   an engaging member, configured to engage a tissue, said engaging member having a first end provided on an outer peripheral face of said outer layer, and a second end extending in a direction of said axis and opening to the outer side of the medical stent in a radius direction of the outer layer, wherein said coil comprises:
- a marker coil part and is formed by winding said wire around said axis;
- a first normal-wound coil part which is connected to a distal end of the marker coil part is formed by winding said wire around said axis; and
- a second normal-wound coil part which is connected to a proximal end of the marker coil part and is formed by winding said wire around said axis,
- wherein each of a pitch of said wire around the axis in said first normal-wound coil part and a pitch of said wire around the axis in said second normal-wound coil part is greater than a pitch of said wire around the axis in said marker coil part, and
- wherein said marker coil part of said coil is provided at a position corresponding to a position of said second end of said engaging member in said direction of said axis.

2. The medical stent according to claim 1, wherein:
said first resin material of said outer layer is one of polyamide elastomer resin, polyethylene elastomer resin, polyethylene resin, polystyrene elastomer, or polyurethane elastomer resin; and
the Shore hardness of the outer layer is 25D or more and 70D or less, and the glass transition temperature of the outer layer is equal to or higher than −40° C.

3. The medical stent according to claim 1, wherein
the flexural module of said outer layer is 5 MPa or more and 700 MPa or less; and
the flexural module of said inner layer is 1000 MPa or less.

4. The medical stent according to claim 1, wherein:
a thickness of the medical stent is 0.20 mm or more and 0.35 mm or less; and,
if Y1 is the maximum bending load (N) obtained in a cantilever stiffness test and X1 is the deflection (mm) when said maximum bending load Y1 was applied, indicator A defined by the following equation (1) is 4.0, or less $$A = \frac{Y1}{X1}. \tag{1}$$

5. The medical stent according to claim 1, wherein:
said wire is formed from a radiopaque material; and
each of the pitch of said wire around the axis in said first normal-wound coil part and the pitch of said wire around the axis in said second normal-wound coil part is in the range of two times or more and twenty times or less the pitch of said wire around the axis in said marker coil part.

6. The medical stent according to claim 1, wherein the pitch of said wire around the axis in said first normal-wound coil part, the pitch of said wire around the axis in said second normal-wound coil part and the pitch of said wire around the axis in said marker coil part are set so that a radiopacity of the first normal-wound coil part and a radiopacity of the second normal-wound coil part are different from a radiopacity of the marker coil part, such that an interface between the marker coil part and the first normal-wound coil part, and an interface between the marker coil part and the second normal-wound coil part can be identified under radioscopy.

7. The medical stent according to claim 6, wherein said first normal-wound coil part is provided to be closer to a distal side of the medical stent than the second end of the engaging member.

8. The medical stent according to claim 6, wherein at least one of:
- the interface between the marker coil part and the first normal-wound coil part, and
- the interface between the marker coil part and the second normal-wound coil part, is a predetermined distance from said second end of said engaging member such that a position of the second end of said engaging member can be identified under radioscopy based on the identification of at least one of the interface between the marker coil part and the first normal-wound coil part, and the interface between the marker coil part and the second normal-wound coil part.

* * * * *